United States Patent [19]

Menconi et al.

[11] Patent Number: 4,874,786
[45] Date of Patent: Oct. 17, 1989

[54] CYANOACETAMIDO-DERIVATIVES HAVING A FUNGICIDAL ACTIVITY

[75] Inventors: Augusto Menconi, Carrara Marina; Giovanni Camaggi, Lodi; Franco Gozzo, San Donato Milanese; Luigi Mirenna, Milan; Carlo Garavaglia, Cuggiono, all of Italy

[73] Assignee: Montedison S.p.A., Milan, Italy

[21] Appl. No.: 36,465

[22] Filed: Apr. 9, 1987

[30] Foreign Application Priority Data

Apr. 15, 1986 [IT] Italy .................. 20081 A/86

[51] Int. Cl.$^4$ ............ A61K 31/10; A61K 31/16; A61K 31/165; C07C 103/00
[52] U.S. Cl. ................... 514/528; 514/520; 514/519; 514/521; 514/588; 514/596; 514/598; 514/646; 514/665; 514/670; 558/391; 558/392; 558/436; 558/437; 558/438; 558/445; 564/38; 564/48; 564/49; 564/52; 564/58; 564/60
[58] Field of Search ............... 558/436, 437, 438, 445; 514/528

[56] References Cited

FOREIGN PATENT DOCUMENTS 2837863 7/1984 Fed. Rep. of Germany ...... 558/445
3327013 7/1985 Fed. Rep. of Germany ...... 558/445
1452256 10/1976 United Kingdom .............. 558/445

Primary Examiner—M. C. Lee
Assistant Examiner—J. Richter

Attorney, Agent, or Firm—Stevens, Davis, Miller & Mosher

[57] ABSTRACT

A method of fighting fungus infections by using compounds having the formula:

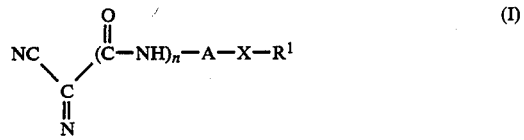

OR wherein:
R is H, a $C_1$-$C_4$ alkyl, an alkenyl, or an alkynyl radical; n is 1 or 2;
A represents a $C_1$-$C_6$ alkylene bridge, an arylene or a heterocyclic bridge;
X represents O, S, SO, $SO_2$; and
$R^1$ is selected from the group consisting of $C_1$-$C_6$ alkyl radicals, a phenyl radical, optionally substituted, polyfluoroalkyl radicals containing from 1 to 4 carbon atoms and at least 2 fluorine atoms, polyfluoroalkenyl radicals containing from 2 to 4 carbon atoms and at least 2 fluorine atoms, but excluding compounds having the formula (I) wherein A is an alkylene radical, n is 2, and $R^1$ is a $C_1$-$C_6$ alkyl radical.

7 Claims, No Drawings

CYANOACETAMIDO-DERIVATIVES HAVING A FUNGICIDAL ACTIVITY

The present invention relates to cyanoacetamido-derivatives having a high fungicidal activity, to a process for the preparation thereof, and to the corresponding employment of such compounds in the field of agriculture.

From British Pat. No. 1,452,256 2-cyano-N-alkylcarbamoyl-2-oxyimino acetamides are known having a fungicidal activity and the following formula:

$$R-O-N=C(CN)-C(O)-NH-C(O)-NHR^1$$

wherein R is a $C_1-C_{13}$ alkyl, a $C_5-C_7$ cycloalkyl or a $C_3-C_6$ alkenyl radical; and $R^1$ is H, a $C_1-C_4$ alkyl or an allyl radical.

From German patent application No. 3,327,013 some compounds are also known having a fungicidal activity and the immediately above indicated formula, wherein, however, R represents H or a $C_1-C_3$ alkyl radical, and $R^1$ represents an alkoxyalkyl radical containing from 3 to 7 carbon atoms.

Moreover from German patent application No. 2,837,863 a series of oxime-derivatives are known, having an antidotic activity and the formula:

$$Q-O-N=C(X)-C(O)-R^1$$

wherein Q, X and $R^1$ have different meanings, among which are the following:
Q=H, and alkyl, an alkenyl, an alkynyl radical;
X=CN; and
$R^1$=NH—CO—$NHR^4$ or $N(R^3)(R^4)$ wherein
$R^3$=H, a lower alkyl radical; and
$R^4$=H, an alkyl, an arylalkyl, an aryl radical, which last may be substituted with a halogen atom, CN, $NO_2$, a lower alkyl, a haloalkyl, or a lower alkoxy radical.

We have discovered a method of fighting fungus infections by using a class of compounds derived from cyanoacetamides, comprising both compounds already known in the prior art, whose fungicidal activity, however, was not known, and compounds that, from a chemical point of view, do not fall within the known formulas of cyanoacetamide derivatives, and that, in comparison with the latter, present a still higher fungicidal activity.

Therefore the object of the present invention is to provide a method of fighting fungus infections in useful plants, consisting in distributing on the plants, on the organs or seeds thereof, when the fungus infection is expected or is already in progress, an effective amount of a compound having the formula:

$$NC-C(=N-OH)-(C(O)-NH)_n-A-X-R^1 \quad (I)$$

wherein:

R is H, a $C_1-C_4$ alkyl, an alkenyl, or an alkynyl radical;
n is 1 or 2;
A represents a $C_1-C_6$ alkylenic bridge, an arylenic or a heterocyclic bridge;
X represents O, S, SO, and $SO_2$; and
$R^1$ is selected from the group consisting of $C_1-C_6$ alkyl radicals, a phenyl radical, optionally substituted, polyfluoroalkyl radicals containing from 1 to 4 carbon atoms and at least 2 fluorine atoms, polyfluoroalkenyl radicals containing from 2 to 4 carbon atoms and at least 2 fluorine atoms, but excluding compounds have the formula (I), wherein A is an alkylene radical, n is 2, and $R^1$ is a $C_1-C_6$ alkyl radical.

A further object of the present invention is to provide a class of compounds falling within above mentioned formula (I), which class of compounds is characterized in that $R^1$ is a polyfluoroalkyl or a polyfluoroalkenyl radical, having the formula:

$$NC-C(=N-)-(C(O)-NH)_n-A-X-R_f \quad (Ia)$$

wherein R, n, A and X have the aforesaid meanings, and $R_f$ represents a polyfluoroalkyl radical containing from 1 to 4 carbon atoms and at least two fluorine atoms or a polyfluoroalkenyl radical containing from 2 to 4 carbon atoms and at least two fluorine atoms.

The compounds having the formula (I) may exist in two stereoisomeric "syn" and "anti" forms; the use of their mixtures in any ratio is to be understood as falling within the spirit of the present invention.

Examples of compounds having the formula (I), which may be used according to the present invention, are reported in Table I.

TABLE 1

$$NC-C(=N-)-(C(O)-NH)_n-A-X-R^1 \quad (I)$$

| Compound No | R | n | A—X—$R^1$ | m. p. °C. |
|---|---|---|---|---|
| 1 | $CH_3$ | 1 | 4-$C_6H_4$—O—$CH_3$ | 133–134 |
| 2 | $CH_3$ | 1 | 3-$C_6H_4$—O—$CH_3$ | 117–118 |
| 3 | $CH_3$ | 1 | 4-$C_6H_4$—O—$CF_2$—$CF_2H$ | 109–110 |
| 4 | $CH_3$ | 2 | 4-$C_6H_4$—O—$CH_3$ | 210–212 |
| 5 | $CH_3$ | 2 | 4-$C_6H_4$—O—$CF_2$—$CF_2H$ | 162–163 |
| 6 | $CH_3$ | 2 | $CH_2$—$CH_2$—O—$CF_2$—$CF_2H$ | 106–107 |

The compounds having the formulae (I) or (Ia), when R=H, are prepared by a reaction of direct nitrosation of cyanoacetamidic derivatives having the formula $$NC-CH_2-(C(O)-NH)_n-A-X-R^1 \quad (II)$$

and, respectively, the formula:

$$\text{NC}\diagdown_{CH_2}\diagup\overset{O}{\underset{\|}{C}}-NH)_n-A-X-Rf \quad \text{(IIa)}$$

by using an alkaline or an alkyl nitrite, preferably an amyl, butyl or propyl nitrite, in the presence of acids or bases, to give rise to oximes having the formula (Ib), according to the equation:

$$\text{(II) or (IIa)} \xrightarrow[H^+ \text{ or base}]{\text{alkyl}-O-NO}$$

$$\text{NC}\diagdown_{\underset{\underset{N}{\|}}{C}}\diagup(\overset{O}{\underset{\|}{C}}-NH)_n-A-X-R^1(\text{or } R^1=Rf)$$
$$\text{OH} \quad \text{(Ib)}$$

Thereupon the other compounds having the formula (I) are easily obtained from oximes (Ib), when R is an alkyl, alkenyl or alkynyl radical, by per se known reactions of alkylation, alkenylation or alkynylation, respectively.

The nitrosation reaction may be carried out in the presence of inorganic bases, such as for instance alkaline hydroxides or carbonates, in a homogeneous or heterogeneous phase, optionally in the presence of phase transfer catalysts or in the presence of sodium hydride or in the presence of organic bases, such as for instance alkaline alcoholates, in an inert alcoholic, or ethereal solvent, or in a solvent consisting of a chloroderivative of a hydrocarbon at a temperature ranging between 0° C. and reflux temperature.

Furthermore it has been discovered to be very convenient, particularly when $R^1$ represents Rf in formula (II), i.e., formula (IIa), to carry out the aforesaid nitrosation reaction in the presence of mineral acids, such as for instance hydrochloric acid or in the presence of organic acids, in an inert solvent, such as for instance tetrahydrofuran, at a temperature ranging between 0° and 50° C.

The cyanoacetamidic derivatives having formula (II) or (IIa) may be prepared by known methods, by using amidation reactions according to one of the following reaction diagrams:

$$\text{NC}\diagdown_{CH_2}\diagup\overset{O}{\underset{\|}{C}}-Cl + \quad \text{(1)}$$

$$H_2N-(\overset{O}{\underset{\|}{C}}-NH)_m-A-X-R^1 \xrightarrow[-HCl]{\text{base}} \text{(II) or (IIa)}$$

wherein m=0 or 1

$$\text{NC}\diagdown_{CH_2}\diagup\text{COOH} + \quad \text{(2)}$$

$$H_2N(\overset{O}{\underset{\|}{C}}-NH)_m-A-X-R^1 \xrightarrow{Ac_2O} \text{(II) or (IIa)}$$
(III)

wherein m=0 or 1

$$\text{NC}\diagdown_{CH_2}\diagup\overset{O}{\underset{\|}{C}}-NH_2 + O=C=N-A-X-R^1 \longrightarrow \quad \text{(3)}$$
(IV)

(II) or (IIa) with n = 2.

The compounds having the formula (IIa) are obtained when $R^1$=Rf in the aforesaid reactions, namely by using in reactions (1) and (2) compounds having the formula:

$$H_2N(\overset{O}{\underset{\|}{C}}-NH)_m-A-X-Rf \quad \text{(IIIa)}$$

wherein m=0 or 1.

Preferably use is made of cyanoacetic acid in the presence of acetic anhydride, according to diagram (2), following a methodology analogous to that described for the preparation of the cyanoacetylureas (Beilstein, vol. 3, page 66, vol. 4, page 67).

The compounds having formula (III) when m=1 and the compounds having formula (IV), are prepared, in their turn, starting from the amines having formula (III), wherein m=0, by using usual methods which are known for the preparation of ureas and isocyanates, respectively.

By way of example, by reacting amines having the formula (III), wherein m=0, with potassium cyanate in the presence of acids, according to Beilstein, Vol. 4, page 286, one easily obtains the ureas having formula (III) with m=1.

The amines of formula (IIIa) when m=0, and having the formula:

$$H_2N\ A-X-Rf \quad \text{(IIIb)}$$

are prepared according to one of the following methods:

(a) addition of aminoalcohols or aminothiols having the formula (V) which, in their turn, are known or may be synthesized by known methods, to fluoroolefins having the formula (VI), according the the equation:

$$H_2N-A-XH + CF_2=C\diagup^{Y^1}\diagdown_{Y^2} \longrightarrow$$
(V) (VI)

$$H_2N-A-X-CF_2-CHY^1Y^2$$
(IIIc)

wherein A has the aforesaid meaning;

$X$=O, S; $Y^1$=F, Cl, $CF_3$; $Y^2$=F, $CF_3$

The reaction is carried out suitably in a solvent of the ethereal kind, such as for instance tetrahydrofuran or in an aprotic polar solvent, such as for instance dimethylformamide, in the presence of a strong base such as sodium hydride or potassium terbutylate, at a temperature ranging between 0° and 100° C., and preferably between 0° and 50° C.

When group A, in the compound having the formula (V), is an arylene or a heterocyclic bridge, it is convenient to protect the aminic group, for instance through formation of a ketiminic bond, that may be hydrolyzed easily when the reaction is over.

The thus-obtained product having the formula (IIIc) may be used either as such or it may be subjected to a dehydrofluorination reaction by means of strong bases in order to obtain the compounds having the formula (IIId) equivalent to formula III wherein m=0, and $R^1$ is a polyfluoroalkenyl group, according to the following equation:

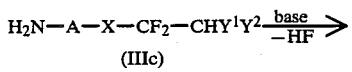
(IIIc)

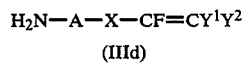
(IIId)

Said reaction of dehydrofluorination may be carried out optionally "in situ", during the preceding reaction of addition.

(b) reaction of aminoalcohols or aminothiols having the formula (V) with a polyfluoroalkylderivative having the formula Rf—Z (VII), wherein Rf is a polyfloroalkyl group as defined hereinbefore and Z represents a leaving group such as, for instance, a bromine atom, a mesylate or tosylate group, according to the following equation:

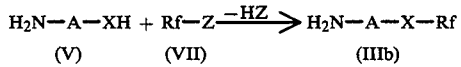

wherein A and Rf have the aforesaid meanings; X=O, S, and Z is a leaving group.

The polyfluoroalkylderivatives having the formula (VII) are known, or they may be easily synthesized starting from compounds such as, for instance, 2,2,2-trifluoroethanol, 2,2,3,3-tetrafluoropropanol, 2,2,3,3,4,4-hexafluorobutanol, and the like.

Alternatively, compounds of the formula (IIIb) may be prepared by reacting a derivative of an aminoalcohol having formula $H_2N$—A—Z (Va), wherein preferably the $NH_2$ group is protected, for instance through a ketiminic bond, with a polyfluoroalcohol or a polyfluorothiol Rf—XH (VIIa) according to the following equation:

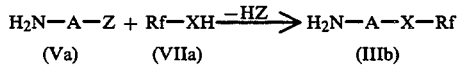

wherein A, Rf and Z have the aforesaid meanings X=O, S, and moreover the fluorine atoms of the Rf group are on carbon atoms which are not situated on position 2 with respect to the —XH group.

In both cases the reaction is carried out in the presence of a strong base, preferably a hydride, a carbonate or an alcoholate of an alkaline metal, and preferably in an inert solvent of the ethereal type such as, for instance, tetrahydrofuran or in an aprotic solvent, for instance, acetonitrile or dimethylformamide, at a temperature ranging between 0° C. and the boiling temperature of the solvent.

Moreover, the above-mentioned reactions described in methods (a) and (b) may be carried out by replacing the aminoalcohols aminothiols having the formula (V), with ureas having the formula (VIII):

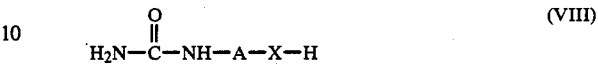

in order to obtain the compounds having formula (IIIa) when m=1.

Ureas (VIII) are known compounds or they may be easily prepared by known methods.

The latter variant is particularly advantageous when the aminic group of the compounds having formula (V) interferes in reactions (a) and (b).

The carbamic group of compounds of formula (VIII), in fact, protects the aminic group.

Moreover, the compounds having formula (I), (II), (III), (Ia), (IIa) and (IIIa), when X=S, may be subjected to oxidation by means of known reactants, such as, for instance, perbenzoic acid or performic acid, in order to obtain the corresponding compounds in the sulfoxidized forms, wherein X=SO or $SO_2$. The compounds having formula (I) are endowed with a considerable fungicidal activity, in particular towards fungi belonging to the Oomiceti class.

They are well tolerated by the plants they act in with systemic activity in applications that may have either a preventive or a curative or an uprooting character.

Furthermore they present, in comparison with known isonitrosocyanoacetoamides, a significantly higher effectiveness as regards protection of plants from the attack of pathogenic fungi.

According to the kind of action desired, such effectiveness shows either through the use of lower doses or through a longer time of effectiveness.

For practical uses in agriculture, it is often useful to have fungicidal compositions at one's disposal containing one or more compounds having the formula (I) as active substance.

The application of such compositions may be carried out on every part of the plant, for instance the leaves, the stalks, the branches or the roots, or on the seeds themselves before sowing or on the soil where the plant grows.

Use may be made of compositions in the form of dry powders, wettable powders, emulsifiable concentrates, pastes, granulates, solutions, suspensions, etc. The choice of the kind of composition will depend on the specific use. The compositions are prepared according to known ways, for instance, by diluting or dissolving the active substance by means of a solvent medium and/or a solid diluent, optionally in the presence of surfactants. As solid diluents or carriers, use may be made of silica, kaolin, bentonite, talc, diatomite, dolomite, calcium carbonate, magnesia, gypsum, clays, synthetic silicates, attapulgite, sepiolite. As liquid diluents, besides water, use may be made of different kinds of solvents, for instance aromatic solvents (benzene, xylols, or mixtures of alkylbenzenes), chloroaromatic solvents (chlorobenzene), paraffins (oil fractions), alcohols (methanol, propanol, butanol), amines, amides (dimethylformamide), ketones (cyclohexanone, acetophenone, isophorone, ethylamylketone), esters (isobutyl acetate).

As surfactants: sodium salts, calcium salts or a triethanolamine of alkylsulfates, alkylsulfonates, alkyl-arylsulfonates, polyethoxylated alkylphenols, fatty alcohols condensed with ethylene oxide, polyethoxylated fatty acids, polyethoxylated sorbitol esters, polyethoxylated fats, ligninfulsonates. The composition may also contain special additives for particular purposes, for instance adhesion agents such as gum-arabic, polyvinyl alcohol, polyvinylpyrrolidone.

If desired, other compatible active substances such as fungicides, phytodrugs, phytogrowth regulators, herbicides, insecticides, fertilizers may be also added to the compositions of the present invention.

The concentration of active substance in the aforesaid compositions may vary over a wide range, according to the active compound, cultivation, pathogen, environmental conditions, and the kind of formulation used. The concentration of active substance generally ranges between 0.1 and 95% and preferably between 0.5 and 90% by weight.

The following examples will illustrate the invention.

EXAMPLE 1

Preparation of 4-tetrafluoroethoxy-aniline 56 g of 4-hydroxy-N-cyclohexylideneaniline, prepared according to known methods, were added, in parts, to a suspension of sodium hydride (3.6 g in an oily suspension at 80%) in a mixture consisting of THF (200 ml, free from hydroquinone) and DMF (150 ml), kept under stirring at 0° C. and under nitrogen.

When the exothermic reaction was over, the temperature of the mixture was permitted to rise again to room temperature and the suspension was stirred for 30 minutes. Then the apparatus was put under vacuum and tetrafluoroethylene was added. The gas absorption (6.9 l) took place over 2 h with a slight exothermicity, that was checked by cooling by means of a water bath at 10° C. Then the reaction mixture was evaporated under vacuum and the thus-obtained residue was poured into water and extracted with ethyl ether. The ethereal extract was treated with aqueous HCl (1:1), at the boiling temperature of the organic solvent, in order to hydrolyze the intermediate imine. The aqueous acid phase was separated, alkalized at pH 10 with NaOH, and extracted with ether. The ethereal extract was dehydrated (Na₂SO₄) and evaporated at reduced pressure and the residue was distilled under vacuum (118°–120° C./0.05 mm Hg) to give 14 g of 4-tetrafluoroethoxy-aniline.

EXAMPLE 2

Preparation of N-(4-tetrafluoroethoxyphenyl)cyanoacetamide 3.1 g of freshly prepared cyanoacetyl chloride were added, drop by drop, to a solution of 4-tetrafluoroethoxyaniline (6.5 g), prepared according to Example 1, in ethylacetate (250 ml), and then the whole was heated to reflux for 30 minutes.

The mixture was cooled to room temperature, the solvent was evaporated at reduced pressure, and the solid residue was mixed with n-hexane, then rinsed with water and dried.

Thus were obtained 6.1 g N-(4-tetrafluoroethoxyphenyl)-cyanoacetamide, m.p. 150°–151° C.

EXAMPLE 3

Preparation of N-(4-tetrafluoroethoxyphenyl) 2-hydroxyiminocyanoacetamide

Gaseous hydrochloric acid was bubbled into a solution consisting of N-(4-tetrafluoroethoxyphenyl)-cyanoacetamide (6 g; Example 2) and n-propylnitrite (14 ml) in THF (10 ml), till a clearly acid pH was reached, while letting the temperature rise to 50° C. Then the mixture was cooled to room temperature, stirred for 2 hours and then permitted to rest overnight. The solvent was evaporated at reduced pressure and the residue was rinsed with n-hexane/ethyl ether to give rise to 3.5 g of N-(4-tetrafluoroethoxyphenyl)2-hydroxyiminocyanoacetamide, m.p. 238°–239° C.

EXAMPLE 4

Preparation of N-(4-tetrafluoroethoxyphenyl)-2-methoxyiminocyanoacetamide (Compound No. 3 in Table 1)

A mixture was prepared consisting of 3.5 g of the hydroxyimino derivative obtained according to Example 3, potassium carbonate (1.52 g), dimethylsulfate (1.38 g), and a catalytic amount of 18-crown-6 ether in acetone (20 ml).

The whole was stirred over 2 hours at room temperature, filtered and the filtrate evaporated at reduced pressure. The solid residue was treated with dichloromethane and the resulting solution was rinsed with water, dried (Na₂SO₄), and evaporated at reduced pressure.

2.1 g of N-(4-tetrafluoroethoxyphenyl)2-methoxyiminocyanoacetamide, m.p. 109°–110° C., were thus obtained.

EXAMPLE 5

Preparation of 2-tetrafluoroethoxy)ethylurea

According to the procedures already described in Example 1, 4.8 l of tetrafluoroethylene were absorbed in the reaction mixture consisting of 2-hydroxyethyl-urea (20.6 g), prepared from ethanolamine according to known methods, and sodium hydride (0.5 g) in 100 ml of anhydrous DMF-THF (1:1).

At the end of the reaction, one cautiously acidified the resulting reaction mixture with concentrated HCl, the solvents were evaporated at reduced pressure, and the residue was treated with 150 ml of 1:1 ethyl ether-ethyl acetate. This was then filtered and the filtrate evaporated at reduced pressure till a constant weight was reached, thereby obtaining 36 g of 2-(tetrafluoroethoxy)ethylurea as a light yellow liquid.

EXAMPLE 6

Preparation of 1-cyanoacetyl-3-(2-tetrafluoroethoxyethyl)urea

A mixture consisting of 2-(tetrafluoroethoxy)ethylurea (20.0 g; Example 5), cyanoacetic acid (8.5), and acetic anhydride (100 ml) was heated slowly up to 70° C. and kept for 2 hours at this temperature. Then the mixture was cooled, evaporated at reduced pressure and the semi-solid residue was filtered and rinsed with ethyl ether.

The raw product (18.3 g) was crystallized from ethyl acetate to give 10 g of 1-cyanoacetyl-3-(2-tetrafluoroethoxyethyl)urea, m.p. 115°–116° C.

EXAMPLE 7

Preparation of 1-(2-hydroxyiminocyanoacetyl)-3-(2-tetrafluoroethoxyethyl)urea This compound, m.p. 164°–165° C., was obtained (11 g) from 1-cyanoacetyl-3-(2-tetrafluoroethoxyethyl)urea (20 g; Example 6), according to the method described in Example 3.

EXAMPLE 8

Preparation of 1-(2-methoxyiminocyanoacetyl)-3-(2-tetrafluoroethoxyethyl)urea (Compound No. 6 in Table 1)

This compound, m.p. 106°–107° C., was obtained (1 g) from 1-(2-hydroxyiminocyanoacetyl)-3-(2-tetrafluoroethoxyethyl)urea (2 g; Example 7), according to the method described in Example 4).

EXAMPLE 9

Preparation of 4-tetrafluoroethoxyphenylurea 10 g of 4-tetrafluoroethoxyaniline, prepared as in Example 1, in 40 ml of water, and 10 ml of 1:1 HCl, were reacted with 3.9 g of potassium cyanate. The mixture was stirred for 30 minutes and the formed solid was filtered out, rinsed with cool water, and dried to give 10.5 g of the desired compound, having a melting point of 167°–168° C.

I.R. and 'HNMR were consistent with the structure as indicated in the title.

EXAMPLE 10

Preparation of 1-cyanoacetyl-3-(4-tetrafluoroethoxyphenyl)urea

According to a procedure analogous to that described above in Example 6, 10.5 g of 4-tetrafluoroethoxyphenylurea were converted into 10.5 g of the title compound. M.P. 205°–206° C. I.R. was consistent with the indicated structure.

EXAMPLE 11

Preparation of 1-(2-hydroxyiminocyanoacetyl)-3-(4-tetrafluoroethoxyphenyl)urea This compound, m.p. 222°–223° C., was obtained according to a process analogous to that described in Example 3, starting from the compound prepared in Example 10 and by using isoamyl nitrite as nitrosation agent. I.R. was consistent with the indicated structure.

EXAMPLE 12

Preparation of 1-(2-methoxyiminocyanoacetyl)-3-(4-tetrafluoroethoxyphenyl)urea (Compound No. 5 in Table 1)

This compound, m.p. 162°–163° C., was obtained according to a process analogous to that described in Example 4, starting from the compound prepared in Example 11.

I.R. and 'HNMR were consistent with the indicated structure.

EXAMPLE 13

Determination of the Preventive Fungicidal Activity Against Plasmopara viticola (B. and C.) Berl. et de Toni Vine leaves cv. Dolcetto, grown in pots in a conditioned environment at 25° C. and 60% R.H., were sprayed on both leaf faces with a water-acetone solution (20% of acetone vol./vol.) containing the products being tested. 1 day or 7 days after the treatment the leaves were sprayed (inoculation) on the lower leaf face with an aqueous suspension of conidia of Plasmopara viticola (200,000 conidia/cc). After a stay of 24 hours in a room saturated with moisture, at 21° C., the plants were removed to 70% R.H. and 21° C. over the incubation period (7 days).

Finally the degree of infection was evaluated by means of indices on a valuation scale ranging from 100 (sound plant) to 0 (completely infected plant).

In Table 2 the results are set forth on the determinations carried out with the compounds of Table 1 that were used in different doses, while carrying out the inoculation 1 day after the treatment.

In Table 3 the activities are reported, in lower doses, of Compound No. 5 of Table 1, compared with reference compound 2-cyano-N-[(ethylamino)carbonyl]-2-(methoxyimino) acetamide, known as Cymoxanil (Curzate). Such activities were evaluated according to the same methodology used for the data of Table 2.

TABLE 2

| Compound No. | Preventive Activity Against Plasmopara viticola On Vine Dose in grams per liter | | | | |
|---|---|---|---|---|---|
| | 0.5 | 0.25 | 0.125 | 0.06 | 0.03 |
| 1 | 100 | 100 | 100 | 100 | 100 |
| 2 | 100 | 100 | 100 | 100 | 60 |
| 3 | 100 | 100 | 100 | 100 | 100 |
| 4 | 100 | 100 | 100 | 100 | 90 |
| 5 | 100 | 100 | 100 | 100 | 100 |
| 6 | 100 | 100 | 100 | 100 | 100 |

Table 3

| Compound No. | Preventive Activity Against Plasmopara viticola On Vine Dose in grams per liter | | | |
|---|---|---|---|---|
| | 0.015 | 0.0075 | 0.037 | 0.0018 |
| 5 | 100 | 100 | 100 | 100 |
| Cymoxanil (Curzate) | 90 | 50 | 25 | 0 |

Some tests were carried out on the preventive fungicidal activity against Plasmopara viticola, according to the above-described methodology, while carrying out the inoculation 7 days after the treatment, by comparing Compound No. 6 of Table 1 in the dose of 0.03 g/l, with Compound Cymoxanil in the dose of 0.03 g/l. From the average of the results it was noted that the vine leaves treated with Compound No. 6 were free from disease, whereas on the leaves treated with the reference compound only 33% of the leaf surface proved to be free from infection.

In Table 4 the preventive activities are reported of Compound No. 5 of Table 1 used in different doses, while carrying out the inoculation 1 day after the treatment, compared with reference compound having the formula (I) wherein R is methyl, n is 2, the group —A—X—R$^1$ is methoxyethyl, that is 1-(2-methoxyimino-cyano-acetyl)3-(2-methoxyethyl) urea according to DOS 3.327.013 Ref. 1.

In Table 5 are reported the preventive activities of Compound No. 6 of Table 1 used in different doses, while carrying out the inoculation 7 days after treatment, compared with reference compound Ref. 1 above-mentioned.

TABLE 4

Preventive Activity Against *Plasmopara viticola* On Vine With The Inoculation 1 Day After The Treatment

| Compound | Dose grams per liter | | |
|---|---|---|---|
| No. | 0.03 | 0.0075 | 0.0018 |
| No. 5 | 100 | 100 | 100 |
| Ref. 1 | 100 | 66 | 20 |

TABLE 5

Preventive Activity Against *Plasmapara viticola* On Vine With The Inoculation 7 Days After The Treatment

| Compound | Dose grams per liter | | |
|---|---|---|---|
| No. | 0.5 | 0.125 | 0.03 |
| No. 6 | 100 | 100 | 100 |
| Ref. 1 | 100 | 100 | 55 |

EXAMPLE 14

Determination Of The Curative Fungicidal Activity Against *Plasmopara viticola* (B and C) Berl. et de Toni Vine leaves CV Dolcetto, grown in pots in a conditioned environment at 25° C. and 60% R.H., were sprayed on the lower leaf face with an aqueous suspension of conidia of *Plasmopara viticola* (200,000 conidia/cc). After a stay of 24 hours in a room saturated with moisture, at 21° C., the plants were sprayed on both leaf faces with a water-acetone solution (20% of acetone vol./vol.) containing the products being tested At the end of the incubation period (7 days) the degree of infection was evaluated at sight by means of indices of a valuation scale ranging from 100 (sound plant) to 0 (completely infected plant).

In Table 6 the curative activities are reported of Compound No. 6 of Table 1 used in different doses, while carrying out the treatment 24 hours after the infection; compared with reference compound Ref. 1 cited in Example 13.

TABLE 6

Curative Activity Against *Plasmopara viticola* On Vine With Treatment 24 Hours After The Infection

| Compound | Dose grams per liter | | |
|---|---|---|---|
| No. | 0.5 | 0.125 | 0.03 |
| No. 6 | 100 | 100 | 100 |
| Ref. 1 | 100 | 73 | 35 |

What is claimed is:

1. Compounds having the formula:

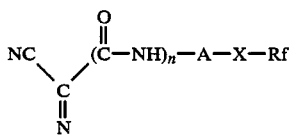

(Ia)

wherein:

R is H, a $C_1$–$C_4$ alkyl, an alkenyl, an alkynyl radical;
n is 1 or 2;
A represents a $C_1$–$C_6$ alkylenic, or an arylenic bridge;
X represents O, S, SO, $SO_2$;
$R_f$ represents polyfluoroalkyl radicals containing from 1 to 4 carbon atoms and at least 2 fluorine atoms, and polyfluoroalkenyl radicals containing from 2 to 4 carbon atoms and at least 2 fluorine atoms.

2. Compound according to claim 1, which is 1-(2-methoxyiminocyanoacetyl)-3-(2-tetrafluoroethoxyethyl)urea.

3. Compounds having the formula:

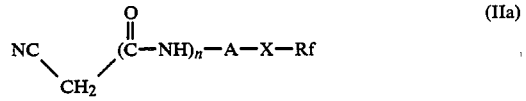

(IIa)

wherein n is 1 or 2; A is an alkylene, an arylene or a heterocyclic bridge; X represents O, S, SO, $SO_2$; Rf represents a polyfluoroalkyl radical containing from 1 to 4 carbon atoms and at least two fluorine atoms, or a polyfluoroalkenyl radical containing from 2 to 4 carbon atoms and at least 2 fluorine atoms.

4. A method of fighting fungus infections in useful plants, consisting essentially in distributing on the plants, or their organs or seeds, when the infection is expected or is already in progress, an effective amount of a compound having the formula:

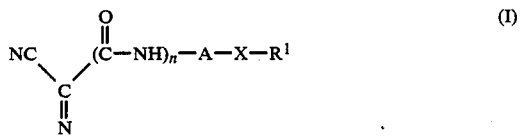

(I)

wherein:

R is H, a $C_1$–$C_4$ alkyl, an alkenyl, an alkynyl radical;
n is 1 or 2;
A represents a $C_1$–$C_6$ alklenic, or an arylenic bridge;
X represents O, S, SO, and $SO_2$; and
$R^1$ represents $C_1$–$C_6$ alkyl radicals, a phenyl radical, polyfluoroalkyl radicals containing from 1 to 4 carbon atoms and at least 2 fluorine atoms, polyfluoroalkenyl radicals containing from 2 to 4 carobn atoms and at least 2 fluorine atoms, but excluding compounds having the formula (I) wherein A is an alkylene, n is 2, and $R^1$ is a $C_1$–$C_6$ alkyl radical.

5. A method of fighting fungus infections in useful plants consisting essentially in distributing on the plant or its seeds or on the soil adjoining the plant, when the fungus infection is expected or is already in progress, an effective amount of a compound according to claim 3, either as such or in the form of a suitable composition.

6. Fungicidal compositions having as active ingredient one or more compounds according to claim 1, together with a solid or liquid carrier.

7. Fungicidal compositions having as active ingredient a compound according to claim 3, together with a solid or liquid carrier.

* * * * *